United States Patent
Lin et al.

(10) Patent No.: US 12,291,497 B2
(45) Date of Patent: *May 6, 2025

(54) 3,3,3',3'-TETRAMETHYL-1,1'-SPIROBIINDANE-7,7'-DIOL

(71) Applicant: ZHEJIANG UNIVERSITY, Hangzhou (CN)

(72) Inventors: Xufeng Lin, Hangzhou (CN); Huanyu Shan, Hangzhou (CN); Qiaoxia Zhou, Hangzhou (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 540 days.

This patent is subject to a terminal disclaimer.

(21) Appl. No.: 17/700,503

(22) Filed: Mar. 22, 2022

(65) Prior Publication Data
US 2022/0213015 A1  Jul. 7, 2022

Related U.S. Application Data

(63) Continuation-in-part of application No. 17/040,550, filed as application No. PCT/CN2018/086893 on May 15, 2018, now Pat. No. 11,377,457.

(51) Int. Cl.
C07C 39/14 (2006.01)
C07C 43/21 (2006.01)

(52) U.S. Cl.
CPC .............. *C07C 39/14* (2013.01); *C07C 43/21* (2013.01); *C07C 2603/40* (2017.05)

(58) Field of Classification Search
CPC .... C07C 39/14; C07C 43/21; C07F 9/657154
See application file for complete search history.

(56) References Cited

FOREIGN PATENT DOCUMENTS

| CN | 1439643 A | * | 9/2003 |
| CN | 1887893 A | * | 1/2007 |

* cited by examiner

*Primary Examiner* — Sikarl A Witherspoon
(74) *Attorney, Agent, or Firm* — Valet Patent Service Limited

(57) ABSTRACT

Provided herein is 3,3,3',3'-tetramethyl-1,1'-spirobiindane-7,7'-diol, which is a compound represented by formula I, or an enantiomer or a raceme thereof. The is prepared with a 3,3,3',3'-tetramethyl-1,1'-spirobiindane-7,7'-diol 3,3,3',3'-tetramethyl-1,1'-spirobiindane-7,7'-dicarbaldehyde derivative as a starting material through a Baeyer-Villiger oxidation rearrangement reaction and an alkaline hydrolysis reaction. The 3,3,3',3'-tetramethyl-1,1'-spirobiindane-7,7'-diol comprises two gem-dimethyl groups and is a key intermediate for preparing corresponding 3,3,3',3'-tetramethyl-1,1'-spirobiindane-based monophosphine ligands, such as phosphonite ligands, phosphite ligands, phosphoramidite ester ligands, phosphoric acid and phsophonamidate. The 3,3,3',3'-tetramethyl-1,1'-spirobiindane-7,7'-diol skeleton provided herein could be used in chemical industry and has economic practicality and industrial application prospects.

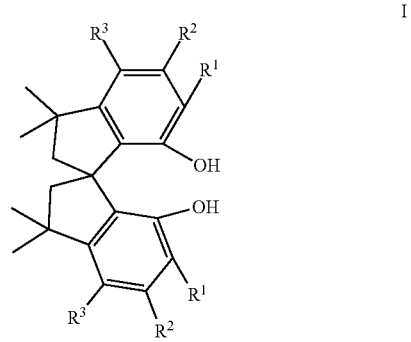

2 Claims, No Drawings

3,3,3',3'-TETRAMETHYL-1,1'-SPIROBIINDANE-7,7'-DIOL

TECHNICAL FIELD

The present application relates to the technical field of organic chemistry, and relates to a novel 3,3,3',3'-tetramethyl-1,1'-spirobiindane-7,7'-diol and a preparation method thereof. The 3,3,3',3'-tetramethyl-1,1'-spirobiindane-7,7'-diol could be used for preparing 3,3,3',3'-tetramethyl-1,1'-spirobiindane-based monophosphine ligand.

BACKGROUND

Asymmetric catalytic synthesis has advantages of chiral proliferation, high enantio-selectivity, economy, and easy industrialization, and could be used as the most direct and effective chemical method for obtaining chiral molecules. Development and discovery of novel and efficient chiral ligands and their catalysts is a pivotal scientific issue in the realization of highly efficient and selective asymmetric catalytic reactions. The searching for novel, high-efficient and high-selective chiral ligands is an eternal theme in asymmetric synthesis. Currently, many excellent chiral ligands or catalysts, as shown in the following structural formulas, have been synthesized, and quite a few of the chiral ligands have been applied in the industrial production. However, none of the chiral ligands is versatile due to the existing problems such as limited applicability of the ligands and high dependence on reaction substrates. For obtaining these ligands, the design and synthesis of a chiral diol or chiral diphenol which is a key intermediate is the most important. Therefore, it is extremely important to design and develop a novel chiral diphenol skeleton.

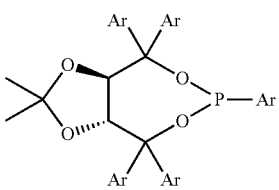

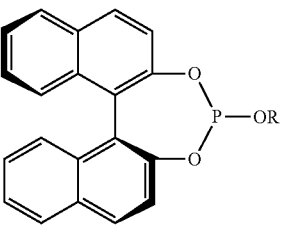

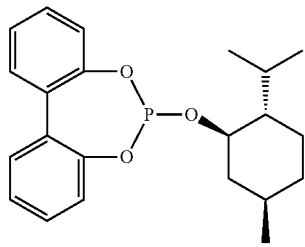

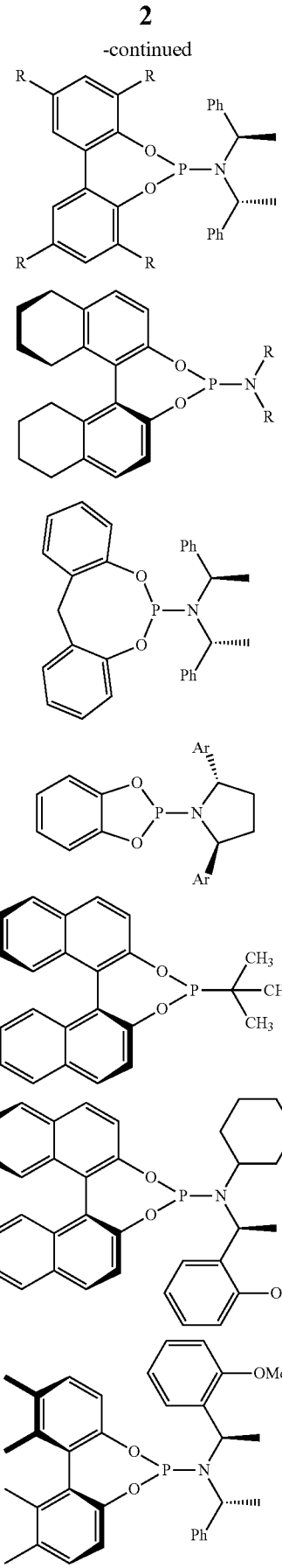

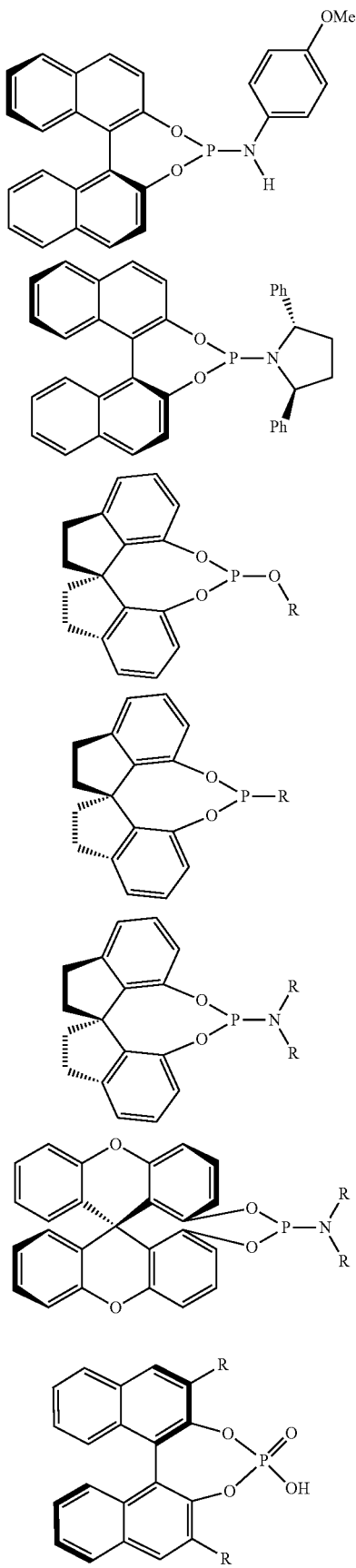
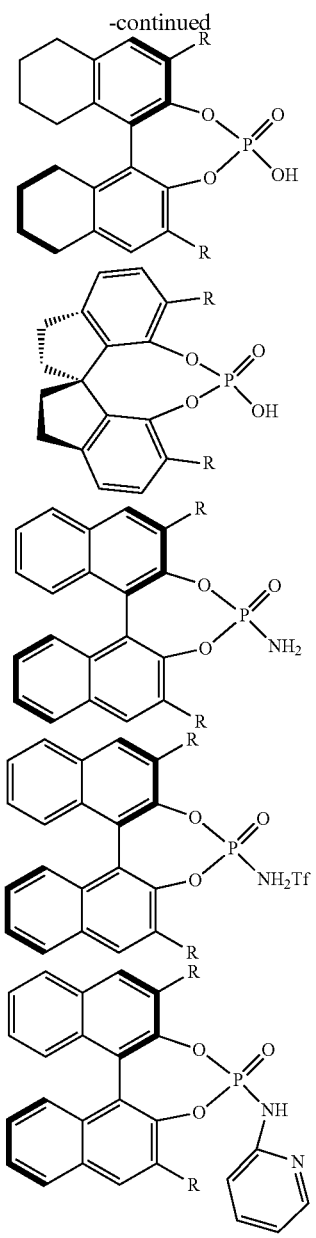

In 1999, Birman et al. synthesized racemic 1,1'-spirobi-indane-7,7'-diol (SPINOL) through a six-step reaction starting from m-methoxybenzaldehyde, and obtained the corresponding optical enantiomer by chemical resolution (Tetrahedron: Asymmetry 1999, 10, 12). However, corresponding 3,3,3',3'-tetramethyl-1,1'-spirobiindane-7,7'-diol and its derivatives having a gem-dimethyl effect cannot be easily obtained according to this reaction scheme or other published methods. Therefore, skeleton reconstruction and new synthetic strategy are required.

It was reported early in 1962 that 3,3,3',3'-tetramethyl-1,1'-spirobiindane-6,6'-diol (MSPINOL) can be directly obtained with high yield through a one-step method from industrialized bisphenol products (such as bisphenol A and bisphenol C) under acid catalysis. Later, modified large scale preparation methods and chiral resolution methods were developed. An exemplary reaction scheme is as below (see J. Chem. Soc., 1962, 415-418; Org. Lett., 2004, 6, 2341-2343; US 2006/0020150; U.S. Pat. No. 4,879,421; and Bull. Chem. Soc. Japan, 1977, 44, 496-505).

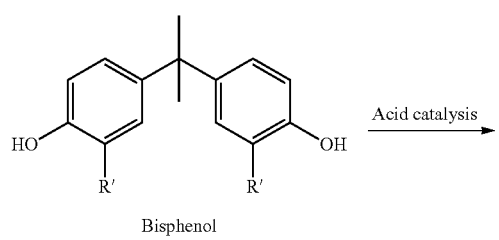

Bisphenol

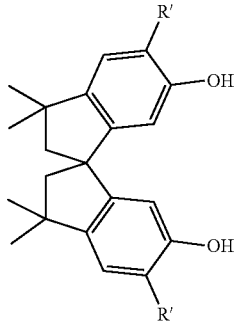

3,3,3',3'-tetramethyl-
1,1'-spirobiindane-6,6'-diol

The present application intends to design and prepare 3,3,3',3'-tetramethyl-1,1'-spirobiindane-7,7'-diol using inexpensive and easily available 3,3,3',3'-tetramethyl-1,1'-spirobiindane-6,6'-diol. The 3,3,3',3'-tetramethyl-1,1'-spirobiindane-7,7'-diol could be used for preparing 3,3,3',3'-tetramethyl-1,1'-spirobiindane-based monophosphine ligands, including phosphonite ligands, phosphite ligands, phosphoramidite ester ligands, phosphoric acid and phsophonamidate. The compound disclosed in the present application has the advantages of cheap and abundant synthetic raw materials, short synthetic routes, low preparation costs, strong practicability, and easy modification.

SUMMARY

An object of the present application is to provide more novel chiral diphenols as skeletons for constructing more novel monophosphine ligands.

Provided herein is 3,3,3',3'-tetramethyl-1,1'-spirobiindane-7,7'-diol, which is a compound represented by formula I, or an enantiomer thereof:

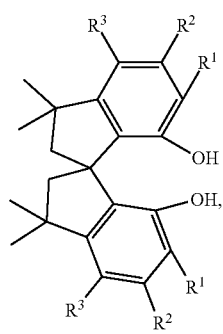

I wherein $R^1$ is selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted arylmethyleneoxy, unsubstituted or substituted heteroarylmethyleneoxy, unsubstituted or substituted aryl, and unsubstituted or substituted heteroaryl; and $R^2$ and $R^3$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl; wherein the substituted aryloxy, the substituted aryl or the substituted heteroaryl has one or more substituents each independently selected from the group consisting of halogen, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl, and the heteroaryl is $C_5$-$C_{14}$ heteroaryl.

The compound represented by formula I may be any one of the following compounds, or an enantiomer or a raceme thereof:

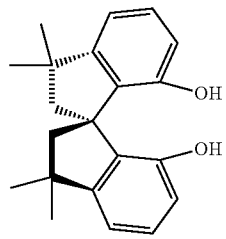

II-a

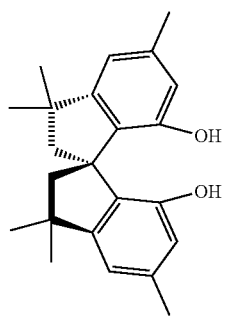

II-b

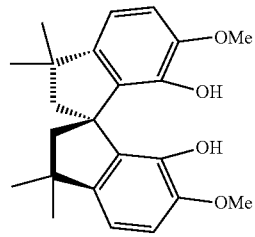

II-c

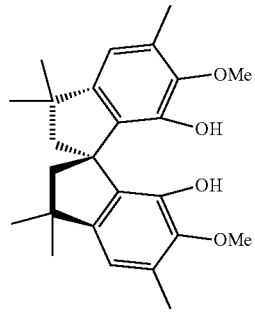

II-d

II-e
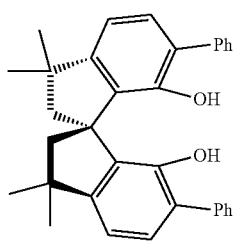

II-f
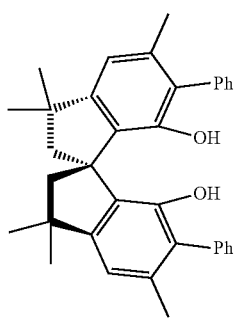

II-g
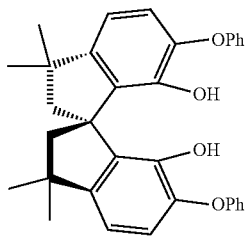

II-h
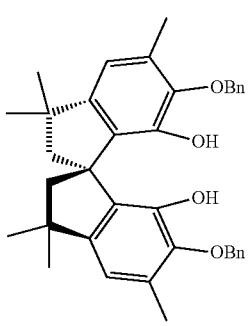

II-i
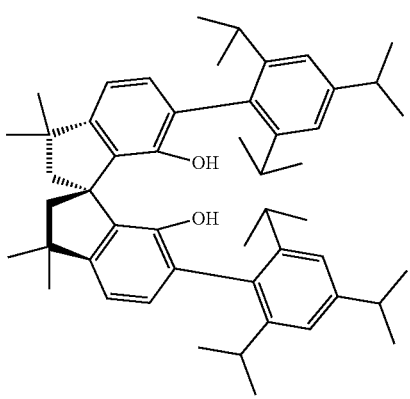

II-j
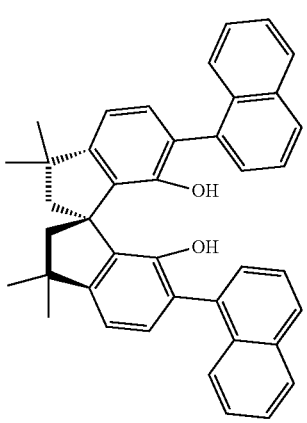

II-k
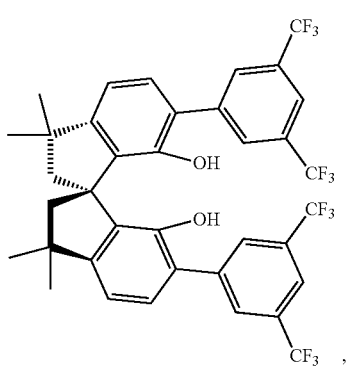

A synthesis method of the 3,3,3',3'-tetramethyl-1,1'-spirobiindane-7,7'-diol compound comprises subjecting a racemic or chiral 3,3,3',3'-tetramethyl-1,1'-spirobiindane-7,7'-dicarbaldehyde derivative (formula III) as a starting material to a Baeyer-Villiger oxidation rearrangement reaction and an alkaline hydrolysis reaction;

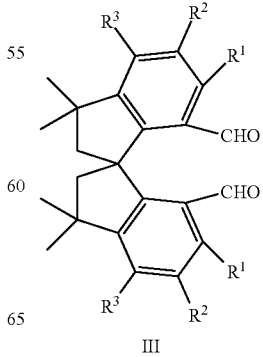

1. Baeyer-Villiger oxidation rearrangement
2. Alkaline hydrolysis

III

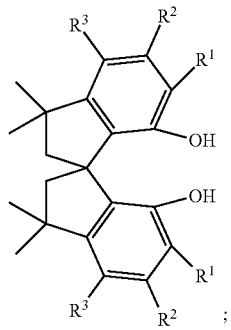

wherein the Baeyer-Villiger oxidation rearrangement reaction is conducted at 0-35° C. for 12-24 hours by using dichloromethane or dichloroethane as a solvent in the presence of a catalyst and an oxidant; the catalyst could be acetic acid, trifluoroacetic acid or a mixed acid thereof, and the molar mass of the acid used is 2-4 times that of the compound of formula III; the oxidant is a peroxyacid, which could be for example, peroxyacetic acid, peroxytrifluoroacetic acid, peroxybenzoic acid, or 3-chloroperoxybenzoic acid, and the molar mass of the peroxyacid used is 2-5 times that of the compound of formula III. After the rearrangement reaction, the product obtained after a conventional post-treatment could be subjected to an alkaline hydrolysis without further purification. The alkaline hydrolysis reaction is performed in a solvent in the presence of an alkali at a temperature of room temperature to 50° C. for 12-24 hours. The alkali used is potassium hydroxide or sodium hydroxide, and the solvent is a mixed solvent of methanol or ethanol and water. After the hydrolysis, the compound of formula I could be obtained through a conventional acidification post-treatment. Wherein the molar mass of sodium hydroxide or potassium hydroxide used is 3-15 times that of the compound of formula III.

The starting material 3,3,3',3'-tetramethyl-1,1'-spirobiindane-7,7'-dicarbaldehyde (formula III) could be prepared according to the method disclosed in PCT/CN2017/119944, entitled 3,3,3',3'-tetramethyl-1,1'-spirobiindane-based bisoxazoline ligand compound, the disclosure of which is incorporated by reference herein in its entirety as part of the present application, and various chiral and racemic 3,3,3', 3'-tetramethyl-1,1'-spirobiindane-7,7'-dicarbaldehyde derivatives could be successfully synthesized by the method disclosed in this patent application.

According to the design of the 3,3,3',3'-tetramethyl-1,1'-spirobiindane-7,7'-diol skeleton in the present application, four methyl groups are added, which are not simple and ordinary unrelated methyl substituents, but are two groups of gem-dimethyl, which greatly change the dihedral angle between the two phenyl groups of the ligand skeleton and the distance between the oxygen atoms of the two phenolic hydroxyl groups in the molecule. It can also be seen from the comparison of monocrystal data that the dihedral angle and the oxygen atomic spacing of 1,1'-spirobiindane-7,7'-diol are 66.69° and 3.393 Å, respectively, while the dihedral angle and the oxygen atomic spacing of 3,3,3',3'-tetramethyl-1,1'-spirobiindane-7,7'-diol are 77.03° and 3.794 Å, respectively. See also *Synthesis*, 2019, 51, 557 (Synthesis and Optical Resolution of 3,3,3',3'-Tetramethyl-1,1'-spirobiindane-7,7'-diol).

The 3,3,3',3'-tetramethyl-1,1'-spirobiindane-7,7'-diol provided herein comprises two gem-dimethyl groups and is a key intermediate for preparing corresponding 3,3,3',3'-tetramethyl-1,1'-spirobiindane-based monophosphine ligands, such as phosphonite ligands, phosphite ligands, phosphoramidite ester ligands, phosphoric acid and phsophonamidate. The novel 3,3,3',3'-tetramethyl-1,1'-spirobiindane-7,7'-diol skeleton provided herein could be used in the chemical industry and has economic practicality and industrial application prospects.

DETAILED DESCRIPTION OF THE EMBODIMENTS

The following examples are provided to facilitate understanding of the present application, but are not intended to limit the scope of the present application.

Example 1

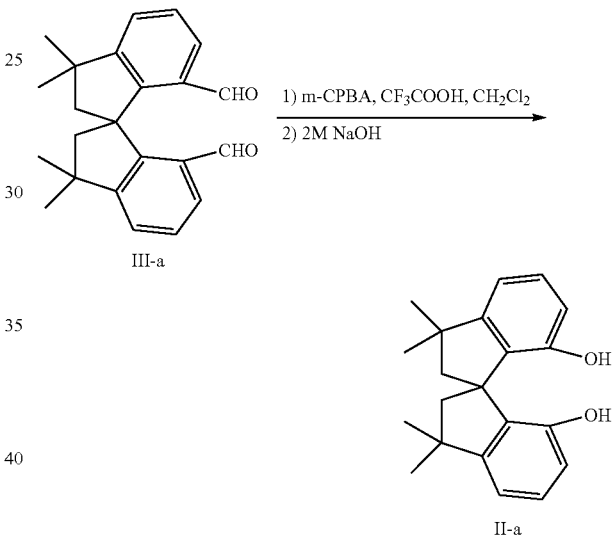

To a three-necked flask, 2 g (6 mmol) of a III-a raceme compound was added, 150 mL of dichloromethane was added under nitrogen protection, the resulting mixture was cooled in an ice bath, and 0.9 mL of trifluoroacetic acid (12 mmol) was added, 4.28 g of m-chloroperoxybenzoic acid (m-CPBA, 27 mmol) was added in three batches, and then the resulting mixture was dissolved by stirring to obtain a reaction solution that was colorless and transparent. After stirring at room temperature overnight for 16 h, the reaction solution became light yellow. The reaction was monitored by a thin-layer chromatography (TLC) plate (color development with 2,4-dinitrophenylhydrazine) until the reaction was completed. 50 mL of saturated sodium sulfite solution was added to quench the reaction, and the organic phase was sequentially washed with water, saturated sodium bicarbonate solution, and saturated sodium chloride solution, dried over anhydrous sodium sulfate, and concentrated to dryness under reduced pressure. The residual solid was dissolved with 10 mL of methanol, and 20 mL of 3 mol/L sodium hydroxide solution was slowly added thereto under stirring, and the resulting mixture was reacted overnight at room temperature. The reaction was monitored by a TLC plate. The reaction solution was acidified to be acidic using 3 mol/L hydrochloric acid at the end of the reaction, and a large amount of white solid precipitated. The resulting reaction solution was extracted with 20 mL of ethyl acetate, the organic phase was washed with saturated sodium chloride solution, and dried over anhydrous sodium sulfate, and the solvent was removed by rotary evaporation under reduced pressure. After purification with silica gel column chromatography (ethyl acetate/petroleum ether=1:10), 1.7 g of product II-a was obtained as a white solid (with a yield of 91%). IR (film): γ=3805, 3746, 3195, 2 983, 2925, 1748, 1683, 1585, 1469, 1456, 1360, 1304, 1242, 1201, 1175. $^1$H NMR (400 MHz, CDCl$_3$) δ 7.21 (m, 2H), 6.83 (d, J=7.5 Hz, 2H), 6.66 (d, J=8.0 Hz, 2H), 4.43 (s, 2H), 2.39 (d, J=13.4 Hz, 2H), 2.33 (d, J=13.4 Hz, 2H), 1.41 (s, 6H), 1.36 (s, 6H). 13C NMR (101 MHz, CDCl$_3$) δ 154.08, 152.71, 130.36, 130.07, 115.41, 114.59, 77.37, 77.05, 76.74, 55.56, 54.14, 44.26, 31.94, 29.68. HRMS (EI, GC-TOF): calcd for $C_{21}H^{24}O_2$ 308.1776, found: 308.1778.

Similarly, by replacing the III-a raceme compound with (R)-III-a compound, a (R)-II-a chiral compound could be obtained with a yield of 90%, $[α]^{20}_D$=−130.1.

Example 2

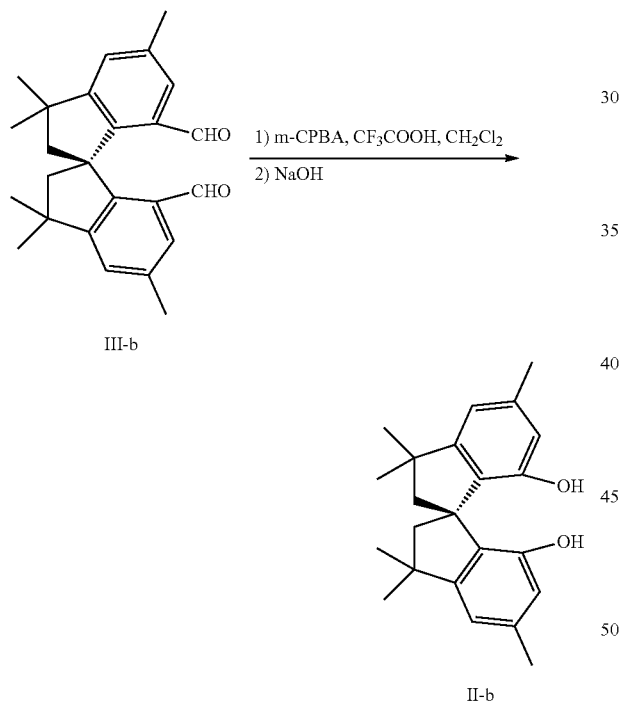

III-b

II-b

To a three-necked flask, 1.44 g of (R)-III-b compound (4 mmol) was added, 150 mL of dichloromethane was added under nitrogen protection, the resulting mixture was cooled in an ice bath, and 3.2 g of m-CPBA (16 mmol) was added in three batches, 0.6 mL trifluoroacetic acid (8 mmol) was added, and then the resulting mixture was dissolved by stirring to obtain a reaction solution that was colorless and transparent. After stirring at room temperature overnight for 15 h, the reaction solution became light yellow. The reaction was monitored by a TLC plate (color development with 2, 4-dinitrophenylhydrazine) until the reaction was finished. 30 mL of saturated sodium sulfite solution was added to quench the reaction, and the organic phase was sequentially washed with water, saturated sodium bicarbonate, and saturated sodium chloride solution, dried over anhydrous sodium sulfate, and concentrated to dryness under reduced pressure. The residual solid was dissolved with 40 mL of methanol, and 16 mL of 1 mol/L sodium hydroxide solution was slowly added thereto under stirring. The resulting mixture was reacted overnight at room temperature for 12 h, and the reaction was monitored by a TLC plate. The reaction solution was acidified to be acidic using 3 mol/L hydrochloric acid at the end of the solution, and a large amount of white solid precipitated. The resulting reaction solution was extracted with 100 mL of dichloromethane, the organic phase was washed with saturated sodium chloride solution, and dried over anhydrous sodium sulfate, and the solvent was removed by rotary evaporation under reduced pressure. After purification with silica gel column chromatography, 1.14 g of product (R)-II-b was obtained as a white solid (with a yield of 82%). Characterization data: m.p. 165-167° C.; $[α]_D^{20}$=−124.8 (c1.0, CH$_2$Cl$_2$); $^1$H NMR (400 MHz, DMSO) δ 6.63 (s, 2H), 6.50 (s, 2H), 4.41 (s, 2H), 2.35 (d, J=13.4 Hz, 2H), 2.30 (m, 8H), 1.38 (s, 6H), 1.33 (s, 6H); $^{13}$C NMR (100 MHz, DMSO) δ 154.0, 152.4, 140.7, 127.1, 116.1, 115.4, 55.9, 53.4, 44.1, 31.9, 29.6, 21.5.

Similarly, by replacing the (R)-III-b compound with the III-b raceme compound, the II-b raceme compound could be obtained with a yield of 80%.

Example 3

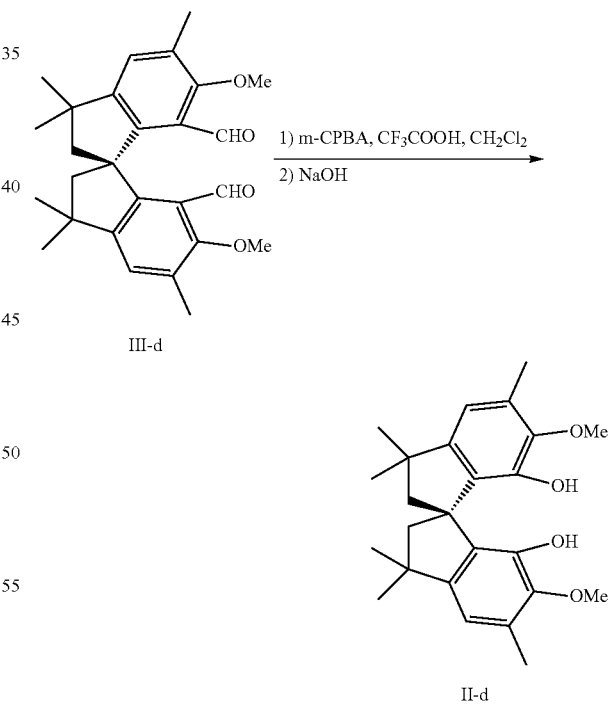

III-d

II-d

The product (R)-II-d was obtained (with a yield of 92%) according to the experimental procedure of Example 2 by replacing the (R)-III-b compound with (R)-III-d. 1H NMR (400 MHz, CDCl$_3$) δ 6.55 (s, 2H), 5.09 (s, 2H), 3.71 (s, 6H), 2.47 (d, J=13.0 Hz, 2H), 2.29 (s, 6H), 2.22 (d, J=13.0 Hz, 2H), 1.37 (s, 6H), 1.31 (s, 6H).

Example 4

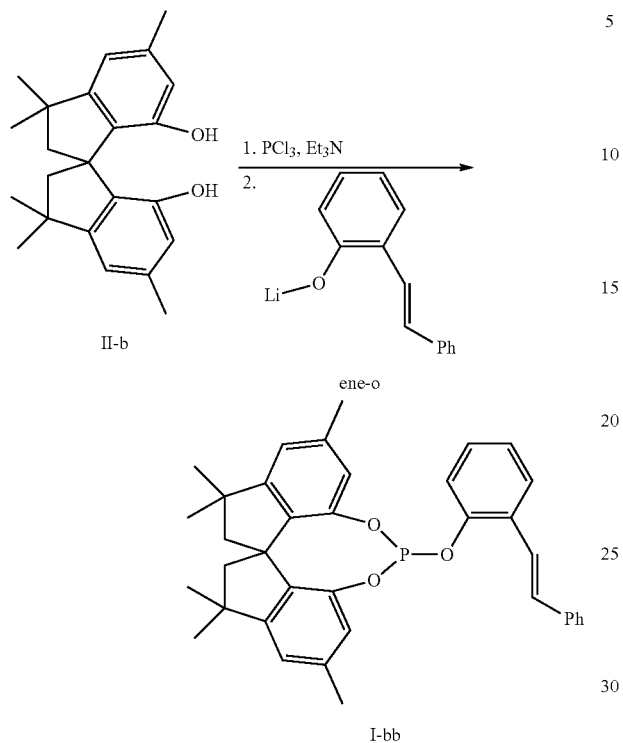

Under the protection of nitrogen, 20 mL of tetrahydrofuran, phosphorus trichloride (1.3 mmol) and triethylamine (2.7 mmol) were added sequentially to a dried round bottom flask. The resulting system was cooled to −78° C., stirred evenly, and 5 mL of II-b (1.25 mmol) solution in tetrahydrofuran was slowly injected thereto, and a large amount of white precipitate was quickly formed. After maintaining the temperature and reacting for 1 h, the temperature was naturally raised to room temperature, and the reaction was continued for 1 h to obtain a suspension. The suspension was filtered with a steel bridge under a condition free of water and oxygen, and the precipitate was removed and washed with 5 mL of tetrahydrofuran to obtain a clear solution of spirophosphinyl chloride. The clear solution was cooled to −78° C., and a solution of o-alkenylphenol lithium salt (ene-o) in THF was added therein, and the resulting mixture was reacted at this temperature for 1 h. Then the temperature was naturally raised to room temperature, and the reaction solution was stirred overnight, and then desolvated under reduced pressure. After purification with column chromatography, the compound I-bb was obtained as a white solid with a yield of 75%. Wherein, the solution of o-alkenylphenol lithium salt in THF was prepared as follows: under nitrogen protection, 5 mL tetrahydrofuran and o-alkenylphenol lithium salt (ene-o) (1.5 mmol) were added to a 10 mL reaction flask, and cooled to 30° C., and a solution of n-butyllithium (1.6 M, 1.5 mmol) in n-hexane was added thereto; the resulting mixture was reacted for 30 minutes at this temperature, then the temperature was naturally raised to room temperature and the solution of o-alkenylphenol lithium salt in THF was obtained.

Similarly, by replacing the II-b raceme compound with the (R)-II-b compound, the (R)-I-bb compound (which could be used as a chiral monophosphine ligand for metal-catalyzed asymmetric reactions) could be obtained with a yield of 70%. Characterization data: white solid, m.p. 60-62° C.; $[\alpha]_D^{20}$=+318 (c0.1, $CH_2Cl_2$); $^1$H NMR (400 MHz, $CDCl_3$) δ 7.71-7.64 (m, 1H), 7.39 (d, J=7.3 Hz, 2H), 7.32 (t, J=7.5 Hz, 2H), 7.28-7.18 (m, 3H), 7.15-7.03 (m, 3H), 6.83 (s, 1H), 6.77 (s, 1H), 6.74 (s, 1H), 6.51 (s, 1H), 2.40 (dd, J=12.5, 10.4 Hz, 2H), 2.33 (s, 3H), 2.14-1.98 (m, 5H), 1.53 (s, 3H), 1.52 (s, 3H), 1.32 (s, 3H), 1.25 (s, 3H).

What is claimed is:

1. A 3,3,3',3'-tetramethyl-1,1'-spirobiindane-7,7'-diol, being a compound represented by formula I, or an enantiomer thereof:

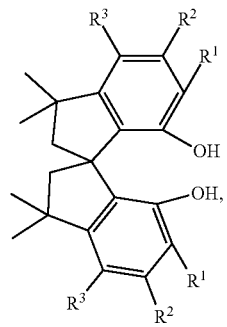

wherein $R^1$ is selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted arylmethyleneoxy, unsubstituted or substituted heteroarylmethyleneoxy, unsubstituted or substituted aryl, and unsubstituted or substituted heteroaryl; and $R^2$ and $R^3$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl; wherein the substituted aryloxy, the substituted aryl or the substituted heteroaryl has one or more substituents each independently selected from the group consisting of halogen, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl, and the heteroaryl is $C_5$-$C_{14}$ heteroaryl.

2. The 3,3,3',3'-tetramethyl-1,1'-spirobiindane-7,7'-diol of claim 1, wherein the compound represented by formula I is any one of the following compounds, or an enantiomer or a raceme thereof:

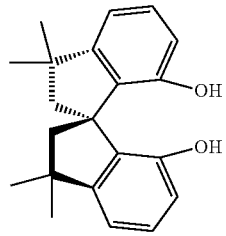

-continued
II-b
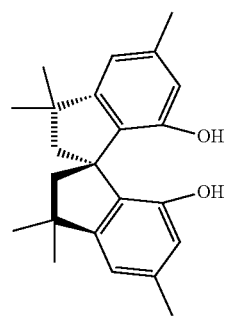
II-c
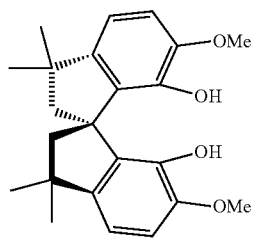
II-d
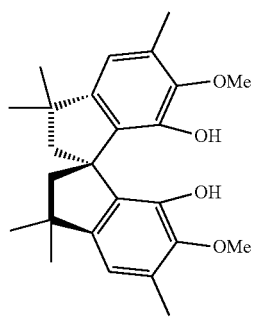
II-e
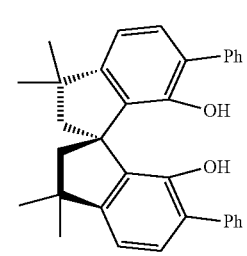
II-f
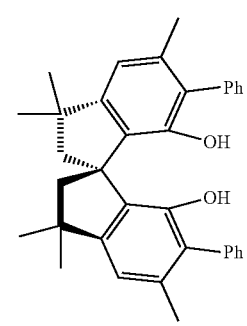
-continued
II-g
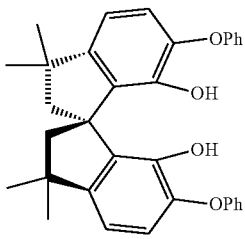
II-h
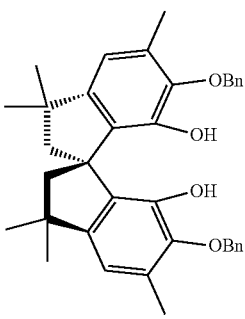
II-i
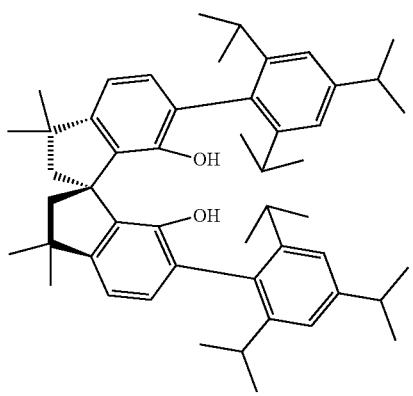
II-j
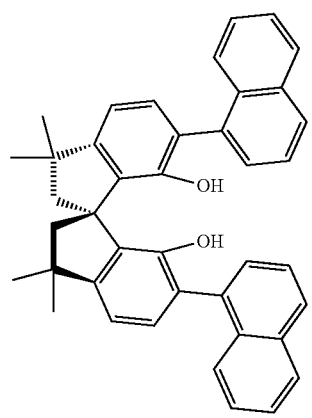

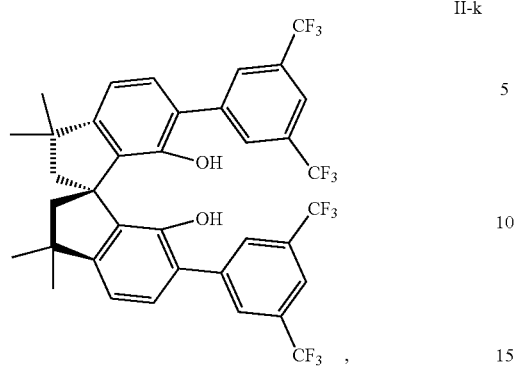
II-k